United States Patent [19]

Toja et al.

[11] Patent Number: 4,829,079
[45] Date of Patent: May 9, 1989

[54] 1-BENZENESULPHONYL-2-OXO-5-ALKOXYPYRROLIDINES AND MEDICAL METHODS OF USE THEREOF

[75] Inventors: Emilio Toja; Carlo Gorini, both of Milan; Carlo Zirotti, Arona; Fernando Barzaghi; Giulio Galliani, both of Monza, Milan, all of Italy

[73] Assignee: Roussel Uclaf, Paris, France

[21] Appl. No.: 947,270

[22] Filed: Dec. 29, 1986

[30] Foreign Application Priority Data

Dec. 30, 1985 [IT] Italy ............................... 23406 A/85
Jul. 11, 1986 [IT] Italy ............................... 21105 A/86

[51] Int. Cl.4 ............... C07D 207/273; C07D 403/12; A61K 31/40
[52] U.S. Cl. .................................. 514/425; 514/343; 546/281; 548/572

[58] Field of Search ................ 548/542; 514/425, 343; 546/281

[56] References Cited

U.S. PATENT DOCUMENTS 3,117,975 1/1964 Boytnick et al. .................... 548/545

FOREIGN PATENT DOCUMENTS 0138721 4/1985 European Pat. Off. .

OTHER PUBLICATIONS

Drugs of the Future, vol. 10, No. 1985, pp. 972, 974.

Primary Examiner—David B. Springer
Attorney, Agent, or Firm—Stevens, Davis, Miller & Mosher

[57] ABSTRACT

Memory enhancing 1-(benzenesulfonyl)-2-oxo-5-alkoxy-pyrrolidines are prepared by alkylation of the corresponding pyrrolidones or pyrrolidone precursors.

10 Claims, No Drawings

1-BENZENESULPHONYL-2-OXO-5-ALKOXYPYRROLIDINES AND MEDICAL METHODS OF USE THEREOF

DESCRIPTION OF THE INVENTION

This invention concerns new derivatives of 1-benzenesulphonyl-2-oxo-5-alkoxypyrrolidine, processes for their preparation, pharmaceutical compositons containing them and a method for using them.

In one aspect the invention relates to compounds having the general formula (I):

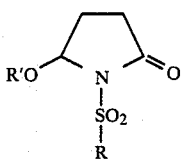

in which R' represents a hydrogen atom, a linear, branched or cyclic alkyl radical containing up to 8 carbon atoms, an alkenyl radical containing from 2 to 8 carbon atoms, an acyl radical containing from 1 to 6 carbon atoms or an aralkyl radical containing from 7 to 15 carbon atoms; and R represents an aryl radical containing up to 14 carbon atoms, possibly substituted, or a possibly substituted mono- or polycyclic aromatic heterocyclic radical.

Preferred alkyl radicals are radicals containing from 1 to 6 carbon atoms, for example, one of the following radicals: methyl, ethyl, n-propyl, isopropyl, n-butyl, isobutyl, tertbutyl, n-pentyl, n-hexyl, cyclopropyl, cyclobutyl, cyclopentyl or cyclohexyl.

Preferred alkenyl radicals are ethenyl, propenyl or butenyl radicals.

Preferred acyl radicals are acetyl, propionyl or butyryl radicals.

Preferred aralkyl radicals are benzyl or phenethyl radicals.

Preferred aryl radicals are phenyl or naphthyl radicals.

Preferred heterocyclic radicals are the following radicals: furyl, pyranyl, pyridyl, benzofuranyl, isobenzofuranyl, chromanyl, isochromanyl, chromenyl, xanthenyl, phenoxathienyl, oxazolyl, isoxazolyl, furazanyl, phenoxazinyl, thieno(2,3-b)-furanyl, 2H-furo(3,2-b)pyranyl, benzoxazolyl or morpholinyl.

When the R radical is substituted, it has as substituents preferably one or more substituents chosen from the group constituted by free, esterified or etherified hydroxyl radicals in which the ester or ether part contains from 1 to 18 carbon atoms, as for example an acetoxy radical, a methoxy radical or a benzyloxy radical; carbonyl and oximino radicals; linear, branched or cyclized alkyl radicals, saturated or unsaturated, containing up to 18 carbon atoms, for example, a methyl, ethyl, propyl or isopropyl radical; an ethenyl radical or an ethynyl radical; halogen atoms, such as fluorine, chlorine, bromine; the following groups: $CF_3$, $SCF_3$, $OCF_3$, $NO_2$, $NH_2$ or $C\equiv N$; a phenyl radical; acyl and alkoxycarbonyl groups containing from 2 to 8 carbon atoms; and alkylsulphonyl groups containing from 1 to 6 carbon atoms.

Pariculary preferred are compounds of the formula (I) in which R represents a phenyl radical possibly substituted by an alkoxy radical containing up to 4 carbon atoms.

Also particularly preferred are compounds of the formula (I) in which R' represents a linear, branched or cyclic alkyl radical containing up to 8 carbon atoms and more particularly an ethyl radical.

Specially preferred is 1-(benzenesulphonyl)-2-oxo-5-ethoxypyrrolidine.

Other preferred compounds are 1-(4-nitrobenzenesulphonyl)-2-oxo-5-ethoxypyrrolidine, 1-(benzenesulphonyl)-2-oxo-5-isopropoxypyrrolidine, and 1-(benzenesulphonyl)-2-oxo-5-propoxypyrrolidine.

The compounds of the invention exhibit useful pharmacological properties: they delay extinction of the conditioned avoidance response and disappearance of the learned response. They improve or enhance mental alertness, memory and the ability to concentrate.

Another aspect of the invention relates to a method for treating intellectual or nervous asthenias and memory failures of old age or of intellectual fatigue with a compound of the formula (I), particularly the compound of Example 1, as well as the compounds of Examples 14, 35 and 36.

The normal posology is variable according to the condition in question, the subject treated and the route of administration. The dosage can comprise between 50 mg and 3000 mg/day, for example, between 150 and 1500 mg/day in one or more doses for the compound of Example 1 administered by the oral route.

In another aspect the present invention relates to pharmaceutical compositions containing as the active principle or ingredient at least one compound of the formula (I). The pharmaceutical compositions of the invention can be solid or liquid and present themselves in the pharmaceutical forms currently used in human medicine, as for example, simple and sugar-coated tablets, capsules, granules, suppositories, injectable preparations; they are prepared according to the usual methods.

The active principle or principles can be incorporated in the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various moisturizing, dispersing or emulsifying agents, and preservatives.

In yet another aspect the invention relates to a process for preparing compounds of the formula (I), characterized in that a compound of the formula (II):

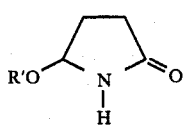

in which R' has the same meaning as previously, is reacted with a compound of the formula (III):

in which Hal represents a chlorine or bromine atom and R has the same meaning as previously, so as to obtain the corresponding compound with the formula (I).

In a preferred means of effecting the process of the invention, the reaction between the product of the formula (II) and the product of the formula (III) is carried out in the presence of a strong base such as butyllithium, an alkaline hydride, such as sodium hydride or sodium bis-(trimethylsilyl)amide; and in a solvent chosen from the group constituted by tetrahydrofuran, benzene, dimethylformamide, dimethylsulphoxide, monoethyl ether of diethylene glycol, or diethyl ether of diethylene glycol.

For the preparation of compounds of the formula (I) in which R represents an aryl radical substituted by one or more amino or hydroxy radicals, the corresponding compounds of the formula (I) in which R represents respectively one or more etherified nitro or hydroxy radicals are reduced. Preferably, the reduction is carried out with hydrogen in the presence of a palladium catalyst in an organic solvent, preferably ethanol.

Compounds of the formula (I), in which R is defined as previously and R' represents a hydrogen atom or an acyl radical containing from 1 to 6 carbon atoms, can be prepared from a halogenide or 4-pentenoyl of the formula (IV):

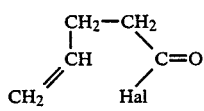
(IV)

in which Hal represents a halogen atom, by reaction in the presence of a condensation agent with a compound with the formula (V):

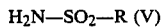

H$_2$N—SO$_2$—R (V)

to obtain a compound of the formula (VI):

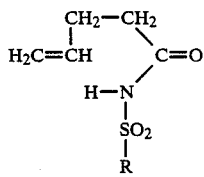
(V)

which is cyclized to obtain the corresponding sulphonamide compound of the formula (I), in which R' represents a hydrogen atom:

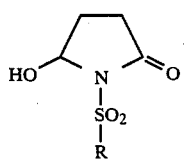
(I)

which is acylated, if desired, to obtain the corresponding compound of the formula (I), in which R' represents an acyl radical:

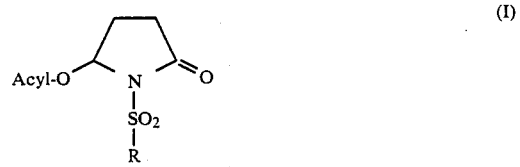

In a preferred way of effecting the above process, the reaction of the compound of the formula (IV) with the compound of the formula (V) is carried out in the presence of phosphorus oxychloride or thionyl chloride. The cyclization of the compound of the formula (VI) is carried out by reaction with osmium tetraoxide and sodium metaperiodate in sequence, or by the action of ozone. Possible reactive substituents of the radical R are protected at the time of condensation and of cyclization, then deprotected afterwards, according to methods known to those skilled in the art.

The compounds of the formula (II) used as starting materials are known compounds which can be prepared according to the process described in Tetrahedron 31, 1437 (1975) or Tetrahedron 41, 2007 (1985). The preparation of other starting materials is described and illustrated in the examples which follow.

The following examples illustrate the invention without limiting it.

Example 1 :
1-benzenesulphonyl-2-oxo-5-ethoxypyrrolidine

To 4.5 g of 5-ethoxypyrrolidin-2-one dissolved in 140 cm$^3$ of anhydrous tetrahydrofuran, 21.8 cm$^3$ of butyllithium in hexane (1.6M) is added drop by drop under an inert atmosphere, while cooling to about −10° C. After 45 minutes, 6.15 g of benzenesulphonyl chloride in tetrahydrofuran is added, and the whole is kept at −10° C. under agitation for 2 hours. It is then returned to ambient temperature, and the residue, after concentrating under reduced pressure, is taken up in 100° ethanol. By cooling and under agitation, the product precipitates, and is then filtered, washed abundantly with water, dried, and 2.8 g of the expected product is obtained after crystallizing from isopropanol, m.p. 112°–113° C.

Analysis

Calculated: C % 53.52, H % 5.61, N % 5.20; Found: 53.30, 5.64, 5.10.

Example 2:
1-(4-methoxybenzenesulphonyl)-2-oxo-5-ethoxypyrrolidine.

By operating as in example 1, starting with 5.2 g of paramethoxy benzenesulphonyl chloride, the expected product is obtained which is chromato-graphed on silica (eluent: benzene-ethyl acetate 5-2), and 1.5 g of the expected product is obtained. M.p. 112°–113° C., after re-crystallizing from isopropanol.

Analysis

Calculated: C % 52.16, H % 5.72, N % 4.68; Found: 52.21, 5.71, 4.62.

Examples 3 to 46:

By operating in a similar manner to that described for example 1 or example 2, the products appearing in the following table have been prepared. In these tables there are shown the physical constants and analyses of the products, as well as the principle characteristics of the operational methods used.

TABLE 1

$$\underset{III}{\text{alcO}}\underset{H}{\overset{}{\bigg\langle}}\hspace{-2pt}\text{N}\hspace{-2pt}=\hspace{-2pt}\text{O} + \text{BuLi} + \text{R SO}_2\text{Hal} \longrightarrow \underset{I}{\text{alcO}}\underset{\text{SO}_2\text{R}}{\overset{}{\bigg\langle}}\hspace{-2pt}\text{N}\hspace{-2pt}=\hspace{-2pt}\text{O}$$

| Ex. | alc | R | + BuLi | + III | Obtaining I | Chromate | solv. cryst. | Yield | F.°C. | Analysis | C% | H% | N% |
|---|---|---|---|---|---|---|---|---|---|---|---|---|---|
| 3 | Et | pyridyl-CH3 | −25° C. 25 mm | −38° C. 20 mm | — | toluene 1 CH3CO2Et 1 | isopropanol | 46% | 59–61 | Calcul. Found | 48.87 48.69 | 5.22 5.08 | 10.36 10.17 |
| 4 | Et | 3,5-(CF3)2-C6H3-CH3 | −40° C. 25 mm | −40° C. t.a. | — | toluene 8 CH3CO2Et 2 | isopropanol | 34% | 77–79 | Calcul. Found | 41.48 41.54 | 3.23 3.14 | 3.45 3.43 |
| 5 | Et | 2-Cl-3-CF3-C6H3-CH3 | −30° C. 30 mm | −30° C. t.a. | +EtOH | — | isopropanol | 42% | 110–111 | Calcul. Found | 42 42.37 | 3.52 3.43 | 3.76 3.69 |
| 6 | Et | 2,3-Cl2-C6H3-CH3 | −20° C. 35 mm | −20° C. t.a. | — | toluene 8 CH3CO2Et 2 | isopropanol | 23% | 104–105 | Calcul. Found | 42.61 42.47 | 3.87 3.77 | 4.14 4.05 |
| 7 | Et | 3-NO2-C6H4-CH3 | −20° C. 40 mm | −20° C. t.a. | — | toluene 8 CH3CO2Et 2 | isopropanol | 22.8% | 83–84 | Calcul. Found | 45.85 46.09 | 4.48 4.61 | 3.91 3.98 |

TABLE 1-continued

Obtaining I: alcO-[pyrrolidinone-NH]=O + BuLi + R SO₂Hal (III) → alcO-[pyrrolidinone-N-SO₂R]=O (I)

| Ex. | alc | R | + BuLi | + III | | Chromate | solv. cryst. | Yield | F.°C. | Analysis | C % | H % | N % |
|---|---|---|---|---|---|---|---|---|---|---|---|---|---|
| 8 | Et | 3-CF₃-C₆H₄ | −15° C. 40 mm | −40° C. ↗ t.a. | — | toluene 2 CH₃CO₂Et 8 | cyclohexane | 23% | 58-59 | Calcul. Found | 46.29 46.08 | 4.18 4.07 | 4.15 4.37 |
| 9 | Et | 3-Cl-C₆H₄ | −15° C. 40 mm | −28° C. 1 h | — | benzene 8 CH₃CO₂Et 2 | isopropanol | 28% | 75-77 | Calcul. Found | 47.44 47.39 | 4.64 4.69 | 4.61 4.55 |
| 10 | Et | 4-F-C₆H₄ | −15° C. 40 mm | −20° C. ↗ t.a. | — | toluene 8 CH₃CO₂Et 2 | isopropanol | 40% | 113-115 | Calcul. Found | 50.16 50.25 | 4.91 4.99 | 4.87 4.86 |
| 11 | Et | 4-Cl-C₆H₄ | −25° C. 40 mm | −25° C. ↗ t.a. | +EtOH ↘ | — | isopropanol | 27% | 120-122 | Calcul. Found | 47.44 47.52 | 4.64 4.66 | 4.61 4.56 |
| 12 | Et | 4-CH₃-C₆H₄ | −15° C. 40 mm | −20° C. ↗ t.a. | — | toluene 8 CH₃CO₂Et 2 | isopropanol | 28.6% | 147-149 | Calcul. Found | 55.10 55.28 | 6.05 6.21 | 4.94 5.12 |
| 13 | Et | 4-(4-C₆H₄-OCH₂)-C₆H₄ | −20° C. 20 mm | −20° C. ↗ t.a. | +H₂O ↘ | toluene 8 CH₃CO₂Et 2 | isopropanol | 28.6% | 147-149 | Calcul. Found | 55.10 55.28 | 6.05 6.21 | 4.94 5.12 |

TABLE 1-continued $$\text{alcO} \underset{H}{\overset{}{\underset{}{\bigcirc}}} \text{N=O} + \text{BuLi} + \text{R SO}_2\text{Hal} \xrightarrow{} \text{alcO} \underset{\text{I}}{\overset{\text{SO}_2\text{R}}{\underset{}{\bigcirc}}} \text{N=O}$$

| Ex. | alc | R | + BuLi | + III | Obtaining I Chromate | solv. cryst. | Yield | F° C. | | Analysis C % | H % | N % |
|---|---|---|---|---|---|---|---|---|---|---|---|---|
| 14 | Et | 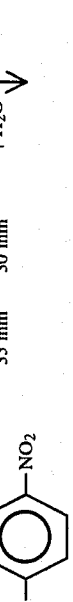 | −20° C. 35 mm | −50° C. 30 mm | +H$_2$O — | EtOH | 51% | 125-126 | Calcul. Found | 45.85 45.93 | 4.48 4.44 | 8.91 9.06 |
| 15 | Et |  | −20° C. 20 mm | −20° C. 1 h | +H$_2$O — | EtOH | 28% | 110 | Calcul. Found | 60.17 68.07 | 5.36 5.22 | 4.38 4.46 |
| 16 | Et | 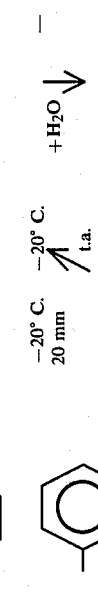 | −20° C. 20 mm | −20° C. t.a. | +H$_2$O — | isopropanol | 39% | 139-140 | Calcul. Found | 60.17 60.12 | 5.36 5.31 | 4.38 4.22 |
| 17 | Et | 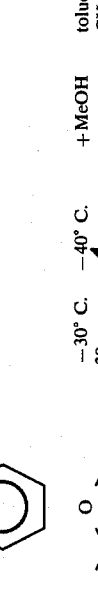 | −30° C. 20 mm | −40° C. t.a. | +MeOH toluene 8 CH$_3$CO$_2$Et 2 | isopropanol | 29% | 74-76 | Calcul. Found | 46.34 46.49 | 5.05 5.04 | 5.40 5.42 |
| 18 | Et | 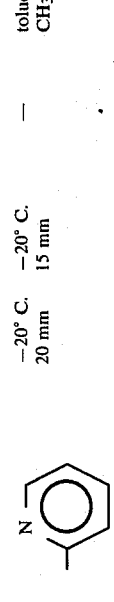 | −20° C. 20 mm | −20° C. 15 mm | — toluene 8 CH$_3$CO$_2$Et 2 | CHCl$_3$ | 10% | 59-60 | Calcul. Found | 48.61 48.69 | 5.16 5.08 | 10.29 10.17 |
| 19 | Et | 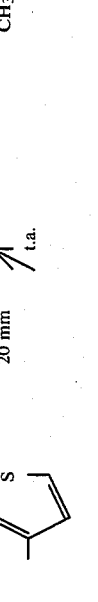 | −25° C. 20 mm | −36° C. t.a. | — toluene 8 CH$_3$CO$_2$Et 2 | isopropanol | 35% | 98-99 | Calcul. Found | 43.62 43.29 | 4.75 4.68 | 5.08 5.16 |

TABLE 1-continued $$\text{alcO} \underset{H}{\overset{N}{\bigcirc}} =O + BuLi + R\,SO_2\,Hal \longrightarrow \text{alcO} \underset{SO_2R}{\overset{N}{\bigcirc}} =O$$
$$\quad\quad\quad\quad\quad\quad\quad III \quad\quad\quad\quad I$$

| | | | Obtaining I | | | | | Analysis | | |
|---|---|---|---|---|---|---|---|---|---|---|
| Ex. | alc | R | + BuLi | + III | Chromate | solv. cryst. | Yield | F.° C. | | C % H % N % |
| 20 | Et | 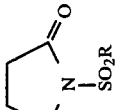 | −20° C. 35 mm | −30° C. 2 h 30 | — | benzene 8 CH₃CO₂Et 2 | isopropanol | 28% | 100–102 | Calcul. Found | 43.57 4.82 5.02 <br> 43.62 4.75 5.08 |
| 21 | Et | 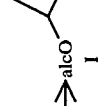 | −20° C. 15 mm | −20° C. 1 h | +H₂O ↓ | — | isopropanol | 18.6% | 100–101 | Calcul. Found | 47.63 4.72 4.53 <br> 47.44 4.64 4.61 |
| 22 | Et | 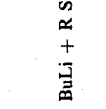 | −20° C. 20 mm | −20° C. ↗ t.a. | — | toluene 8 CH₃CO₂Et 2 | isopropanol | 22.6% | 98–100 | Calcul. Found | 45.85 4.48 8.91 <br> 46.01 4.39 8.83 |
| 23 | Et | 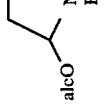 | −20° C. 15 mm | −35° C. 1 h | +H₂O ↓ CHCl₃ | toluene 8 CH₃CO₂Et 2 | isopropanol | 36% | 89–90 | Calcul. Found | 62.48 5.69 4.31 <br> 62.58 5.54 4.05 |
| 24 | Et |  | −23° C. 20 mm | −27° C. ↗ t.a. | EtOH ↓ | — | isopropanol | 25.5% | 106–107 | Calcul. Found | 56.54 6.43 4.71 <br> 56.32 6.39 4.59 |
| 25 | Et |  | −25° C. 20 mm | −37° C. ↗ t.a. | EtOH ↓ | — | isopropanol | 35% | 100–102 | Calcul. Found | 56.54 6.43 4.71 <br> 56.31 6.50 4.65 |

TABLE 1-continued $$\text{alcO}\underset{H}{\overset{}{\underset{N}{\bigcirc}}}\!\!=\!\!O + \text{BuLi} + \text{R SO}_2 \text{ Hal} \xrightarrow{} \text{alcO}\underset{\underset{SO_2R}{N}}{\overset{}{\bigcirc}}\!\!=\!\!O$$
$$\phantom{xxxxxxxxxxxxxxxxxxxxxxxxx} III \phantom{xxx} I$$

| Ex. | alc | R | + BuLi | + III | Obtaining I Chrom. | solv. cryst. | Yield | F.°C. | Analysis C% H% N% | | |
|---|---|---|---|---|---|---|---|---|---|---|---|
| 26 | Et | 3-OCH₃-C₆H₄ | −35° C. 20 mm | −35° C. ↗ t.a. | toluene 8 CH₃CO₂Et 2 | — | 43% | — | Calcul. Found | 52.16 5.72 51.88 5.66 | 4.67 4.56 |
| 27 | Et | 3-SO₂CH₃-C₆H₄ | −20° C. 35 mm | −25° C. 1 h | +H₂O | EtOH | 17.7% | 153-154 | Calcul. Found | 45.12 4.96 44.96 4.98 | 4.22 4.03 |
| 28 | Et | 3-COCH₃-C₆H₄ | −20° C. 15 mm | −20° C. 1 h | +H₂O →CHCl₃ toluene 6 CH₃CO₂Et 4 | isopropanol | — | — | Calcul. Found | 54.00 5.50 54.12 5.48 | 4.50 4.37 |
| 29 | Et | 3-CO₂CH₃-C₆H₄ | −28° C. 20 mm | −42° C. ↗ t.a. | EtOH ↓ | isopropanol | 29% | 101-102 | Calcul. Found | 51.36 5.23 51.43 5.17 | 4.27 4.16 |
| 30 | Et | 3-F-C₆H₄ | −30° C. 20 mm | −38° C. ↗ t.a. | — | isopropanol | 33.6% | 57-59 | Calcul. Found | 50.16 4.91 49.94 4.93 | 4.87 4.73 |
| 31 | Et | 4-biphenyl | −25° C. 20 mm | −35° C. ↗ t.a. | toluene 8 CH₃CO₂Et 2 | isopropanol | 36% | 117-120 | Calcul. Found | 62.58 5.54 62.77 5.39 | 4.05 3.97 |

TABLE 1-continued $$alcO-\underset{H}{N}=O + BuLi + R\,SO_2\,Hal \xrightarrow{III} alcO-\underset{SO_2R}{N}=O$$

| Ex. | alc | R | + BuLi | + III | Obtaining I Chromate | solv. cryst. | Yield | F° C. | Analysis C % H % N % |
|---|---|---|---|---|---|---|---|---|---|
| 32 | Et | 2-CF₃-C₆H₄ | −35° C. 20 mm | −35° C. ↗ t.a. | — | isopropanol | 29% | 94-94 | Calcul. 46.29 4.18 4.15<br>Found 46.41 4.21 4.19 |
| 33 | Et | 4-CF₃-C₆H₄ | −30° C. 20 mm | −35° C. ↗ t.a. | EtOH/H₂O ↘ | toluene 8 CH₃CO₂Et 2 | 26% | 99-101 | Calcul. 46.29 4.18 4.15<br>Found 46.04 4.32 4.06 |
| 34 | CH₃ | C₆H₅ | −10° C. 30 mm | −27° C. ↗ t.a. | +CH₃OH ↘ | isopropanol | 28% | 121-123 | Calcul. 51.75 5.13 5.49<br>Found 52.03 5.24 5.58 |
| 35 | −CH(CH₃)₂ | C₆H₅ | −10° C. 30 mm | −27° C. ↗ t.a. | +H₂O ↘ | EtOH | 61% | 158-160 | Calcul. 55.10 6.05 4.94<br>Found 55.26 6.17 5.01 |
| 36 | −(CH₂)₂CH₃ | C₆H₅ | −18° C. 30 mm | −30° C. ↗ t.a. | — | cyclohexane 1 ether iso 1 | 61% | 63.65 | Calcul. 55.10 6.05 4.91<br>Found 55.29 6.03 4.79 |
| 37 | −CH(CH₃)₂ | 4-NO₂-C₆H₄ | −35° C. 20 mm | −35° C. ↗ t.a. | +H₂O ↘ | CH₃CO₂Et 1 n-hexane 2 | 42.9% | 153-154 | Calcul. 47.55 4.91 8.53<br>Found 47.39 4.88 8.61 |
| 38 | −CH(CH₃)₂ | 4-C₆H₅-C₆H₄ | −35° C. 30 mm | 35° C. 30 mm | +H₂O ↘ | EtOH | 43.02% | 135-137 | Calcul. 63.49 5.89 3.90<br>Found 63.41 5.83 3.97 |

TABLE 1-continued $$\text{alcO} \underset{H}{\overset{}{\underset{\displaystyle N}{\bigcirc}}} = O + \text{BuLi} + \text{R SO}_2 \text{Hal} \xrightarrow{III} \text{alcO} \underset{\underset{\displaystyle SO_2R}{\displaystyle N}}{\overset{}{\underset{\displaystyle}{\bigcirc}}} = O$$

| Ex. | alc | R | + BuLi | + III | | Obtaining I Chromate | solv. cryst. | Yield | F.°C. | | Analysis C% H% N% |
|---|---|---|---|---|---|---|---|---|---|---|---|
| 39 | —(CH₂)₃CH₃ | phenyl | −47° C. 30 mm | −47° C. ↙ t.a. | — | CH₃CO₂Et | ether iso. n-hexana | 31.70% | 46-48 | Calcul. Found | 56.54 6.44 4.71 / 56.61 6.39 4.68 |
| 40 | cyclopentyl | phenyl | −32° C. 20 mm | −32° C. ↙ t.a. | +H₂O → | — | (1) isopropanol (2) EtOH | 54.7% | 96-97 | Calcul. Found | 58.23 6.19 4.53 / 58.05 6.16 4.76 |
| 41 | cyclohexyl | phenyl | −32° C. 20 mm | −32° C. ↙ t.a. | +H₂O → | — | (1) isopropanol (2) EtOH | 28% | 108-109 | Calcul. Found | 59.42 6.54 4.33 / 59.21 6.66 4.29 |
| 42 | —(CH₂)₄CH₃ | phenyl | −35° C. | −40° C. ↙ t.a. | — | CH₃CO₂Et 1 n-hexane 2 | — | 75.7% | — | Calcul. Found | 57.85 6.80 4.50 / 58.02 6.74 4.63 |
| 43 | —(CH₂)₅CH₃ | phenyl | −35° C. | −40° C. ↙ t.a. | — | CH₃CO₂Et 1 n-hexane 2 | — | 32% | eb 250° C. 0.08mbar | Calcul. Found | 59.05 7.12 4.30 / 58.94 6.99 4.15 |
| 44 | —CH₂CH(CH₃)₂ | phenyl | −35° C. 20 mm | −45° C. ↙ t.a. | — | CH₃CO₂Et 1 n-hexane 2 | — | 67.2% | 70-71 | Calcul. Found | 57.85 6.80 4.71 / 58.02 6.74 4.76 |
| 45 | —CH(CH₃)₂ | 4-methoxyphenyl | −35° C. 20 mm | −45° C. ↙ t.a. | +H₂O → | — | isopropanol | 52.9% | 97-98 | | 56.54 6.44 / 56.36 6.51 |

TABLE 1-continued $$\underset{H}{\overset{alcO}{\bigg\langle}}\underset{H}{\overset{N}{\bigg\rangle}}=O + BuLi + R\,SO_2Hal \longrightarrow \underset{I}{\overset{alcO}{\bigg\langle}}\underset{SO_2R}{\overset{N}{\bigg\rangle}}=O$$
III

| | | | | Obtaining I | | | | Analysis |
|---|---|---|---|---|---|---|---|---|
| Ex. | alc | R | + BuLi | + III | Chromate | solv. cryst. | Yield | F.° C. | C % H % N % |
| 46 | —CH(CH₃)₂ |  CF₃ | −35° C. 20 mm | −45° C. ↗ t.a. | +H₂O ↓ | — | — | 24.4% | 101-102 |
| 46 | —CH(CH₃)₂ |  CF₃ | −35° C. 20 mm | −45° C. ↗ t.a. | +H₂O ↓ | — | — | — | |

Example 47:
1-(4-hydroxybenzenesulphonyl)-2-oxo-5-ethoxypyrrolidine.

At 20° C., and under 1000 mbar, 6.3 g of 1-(4-benzyloxyphenylsulphonyl)-5-ethoxypyrrolidin-2-one is hydrogenated in the presence of 1.2 g of catalyst (Pd at 10%), in 150 cm$^3$ of 96° ethanol. After filtering, concentrating the filtrate, and crystallizing the residue from 96° ethanol, 2.5 g of the expected product is obtained, m.p. 162°–163° C.

Analysis

Calculated: C % 50.51, H % 5.30, N % 4.90; Found: 50.70, 5.21, 5.01.

Example 48:
1-(4-aminobenzenesulphonyl)-2-oxo-5-ethoxypyrrolidine.

At ambient temperature and pressure, 4.5 g of 1-(4-nitrophenylsulphonyl)-5-ethoxypyrrolidin-2-one, dissolved in 200 cm$^3$ of 96° ethanol is hydrogenated in the presence of palladium at 10% on charcoal. The insoluble matter is filtered off and taken up with hot chloroform, filtered, and the last filtrate is added to the alcohol solution resulting from the first filtration. After re-crystallizing the residue twice from 96° ethanol, 2.3 g of the expected product is obtained, m.p. 185°–186° C.

Analysis

Calculated: C % 50.69, H % 5.67, N % 9.85; Found: 50.45, 5.57, 9.79.

Example 49:
1-benzenesulphonyl-2-oxo-5-benzyloxypyrrolidine

At ambient temperature and under an inert atmosphere, 4.40 g of 5-benzyloxypyrrolidin-2-one is added to a solution of 4.64 g of sodium bis(trimethylsilyl) amide in 350 cm$^3$ of anhydrous ethyl ether. The mixture is agitated for 30 minutes, then cooled to 0° C., and a solution of 4.06 g of benzenesulphonyl chloride in 30 cm$^3$ of anhydrous ether is added, while maintaining the temperature at 0° C. The temperature is allowed to return to the ambient, then, after filtering and evaporating the solvent under reduced pressure, the residue is chromatographed on silica, eluting with a mixture of ethyl acetate and n-hexane (1-2). After re-crystallizing from a mixture of benzene and n-hexane (1-3), 2.25 g of the expected product is obtained, m.p. 80°–81° C.

Analysis $C_{17}H_{17}NO_4S$ Calculated: C % 61.61, H % 5.17, N % 4.23; Found: 61.39, 5.23, 4.31.

Example 50:
1-benzenesulphonyl-2-oxo-5-(propen-2-yloxy)pyrrolidine

The operation is done as in example 49, starting with 0.80 g of 5-(2-propenyloxy)pyrrolidin-2-one. After cooling to −10° C., a solution of 1.00 g of benzenesulphonyl chloride in 10 cm$^3$ of anhydrous ether is added and the temperature is maintained at −10° C. 100 cm$^3$ of ethyl acetate is added before filtering. Elution is done with a mixture of ethyl acetate and hexane (1-1) and by re-crystallizing from isopropyl ether, 0.20 g of product is obtained, m.p. 54°–56° C.

Analysis $C_{13}H_{15}NO_4S$ Calculated: C % 55.50, H % 5.37, N % 4.98; Found: 55.62, 5.28, 5.01. Preparation of 5-(2-propenyloxy)pyrrolidin-2one).

2.5 g of 5-hydroxypyrrolidin-2-one and 1.25 g of Amberlite IR 120 (H) resin are heated to 65° C. for 1 hour 30 minutes in 55 cm$^3$ of allyl alcohol. After allowing to return to ambient temperature, the alcohol is evaporated under reduced pressure and the residue is chromatographed on silica, eluting with ethyl acetate. 0.90 g of the expected product is obtained.

Analysis $C_7H_{11}NO_2$ Calculated: C % 59.56, H % 7.85, N % 9.92; Found: 57.81, 7.75, 9.10.

Example 51:
1-benzenesulphonyl-2-oxo-5-hydroxypyrrolidine 50 mg of osmium tetraoxide is added to a solution of 5 g of N-benzenesulphonyl-4-pentenoylamide in 150 cm$^3$ of dioxan and 50 cm$^3$ of water. After about 20 minutes, 5.10 g of sodium metaperiodate is added, and after agitating for 1 hour, a further 5.10 g of sodium metaperiodate is added, with agitation for a further 2 hours at ambient temperature. The precipitate formed is filtered off, the filtrate is evaporated to dryness and the residue is dissolved in 50 cm$^3$ of ethyl acetate, treated with activated charcoal, then evaporated to dryness. The residue is triturated in anhydrous ethyl ether, and 2.05 g of the expected product is obtained, which is re-crystallizxed from isopropanol m.p. 121° C.

Analysis $C_{10}H_{11}NO_4S$, MW: 241.27; Calculated: C % 49.78, H % 4.59, N % 5.80; Found: 49.69, 4.46, 5.89.

The N-benzenesulphonyl-4-pentenoylamide used in example 51 has been prepared as follows.

2.4 g of 4-pentenoyl chloride (Tetrahedron 32, 1085 (1976)) and 2.65 g of benzenesulphonamide in 5 cm$^3$ of phosphorus oxychloride are agitated for 20 hours at ambient temperature. The solution obtained is evaporated carefully to dryness under reduced pressure, and 4 g of the expected product is obtained. This product is used as it is.

Example 52:
1-benzenesylfonyl-2-oxo-5-acetoxypyrrolidine.

2.90 g of 1-benzenesulphonyl-5-hydroxypyrrolidin-2-one is heated to reflux for one-and-a-half hours in 58 cm$^3$ of acetic anhydride. After allowing this to cool to ambient temperature, the solvent is evaporated under reduced pressure while forming the azeotrope acetic anhydride-toluene. The residue is crystallized from 95° ethanol, and 2.45 g of the expected product is obtained, m.p. 153°–155° C.

Analysis $C_{12}H_{13}NO_5S$, MW: 283.31; Calculated: C % 50.85, H % 4.62, N % 4.94; Found: 51.04, 4.49, 5.12. Preparation of the 5-isopropoxy pyrrolidin-2-one used as starting materials in examples 35 and 37.

28.64 g of succinimide in 1200 cm$^3$ of isopropanol is cooled to −10° C., 32.80 g of sodium borohydride is added, with agitation for four hours, while the temperature is kept between −10° C. and 0° C. and while adding every 15 minutes 15 drops of a 2N solution of hydrochloric acid in isopropanol. Then, between 0° and 2° C., the ph is adjusted to 2–3 by adding a 2N solution of hydrochloric acid in isopropanol, and agitation is continued for 2 hours at this temperature. Finally, at 0° C., the solution is neutralized by means of a solution of potassium hydroxide in isopropanol. The solvent is evaporated under reduced pressure, extraction is done with chloroform, the extracts are concentrated to dryness under reduced pressure, and 20.5 g of the expected product is obtained, m.p. 68°–71° C. Preparation of the 5-propoxy pyrrolidin-2-one used as starting materials in example 36.

The operation is done in a similar manner, with n-propanol instead of isopropanol. 16 g of sodium borohydride is used and cooled to −7°–0° C. 27.50 g of the expected product is obtained, m.p. 52°–54° C. Preparation of the 5-methoxy pyrrolidin-2-one used at the start of example 34 and of the 5-butoxy pyrrolidin-2-one used at the start of example 39. Synthesis (4) 315-317 (1980) (technique with sodium borohydride). Preparation of the benzyloxyphenylsulphonyl used as starting materials in example 13

(a) Sodium benzyloxyphenylsulphonate

For 30 minutes at ambient temperature, 30 g of the sodium salt of bihydrated paraphenolsulphonic acid is agitated in 49 cm$^3$ of a 15% aqueous solution of sodium hydroxide. A solution of 27.95 g of benzyl bromide in 60 cm$^3$ of ethanol is added, and the whole is heated to reflux for 5 hours. After leaving to rest for one night, 34.3 g of the expected product is filtered off.

(b) Benzyloxyphenylsulphonyl chloride 34.3 g of the product obtained above is mixed with 430 cm$^3$ of methylene chloride, 24.95 g of phosphorus pentachloride is added and the whole is heated to reflux for 7 hours. It is then taken to dryness under reduced pressure and extracted with anhydrous toluene. The solvent is evaporated off and the residue is recrystallized from isopropyl ether and filtered hot on activated charcoal. 23.95 g of the expected product is obtained, m.p. 101°–103° C. Preparation of 5-isobutoxy pyrrolidin-2-one.

2.5 g of 5-hydroxy pyrrolidin-2-one and 1.25 g of Amberlite resin IR-120 (H) are heated to 65° C. for 3 hours in 55 cm$^3$ of isobutanol. After allowing to return to ambient temperature, filtering off the resin and distilling off the solvent under reduced pressure, a residue is obtained which is chromatographed on silica, eluting with ethyhtgl acetate, and 2.90 g of the expected product is obtained, m.p. 30°–32° C.

Analysis $C_8H_{15}NO_2$ Calculated: C % 61.12, H % 9.62, N % 8.91; Found: 60.87, 9.54, 8.83.

5-pentyloxy pyrrolidin-2-one, 5-cyclopentyloxy pyrrolidin-2-one, 5-benzyloxy pyrrolidin-2-one, 5-hexyloxy pyrrolidin-2-one, 5-cyclohexyloxy pyrrolidin-2-one: these products have also been prepared as above, by using Amberlite resin and the appropriate alcohol. (See following table).

Examples of pharmaceutical compositions (a) Tablets have been prepared responding to the following formula:
Product of example 1; 100 mg
Excipient q.s. for a tablet finished at; 300 mg
(Detail of excipient: lactose, corn starch, treated starch, rice starch, magnesium stearate, talc).

(b) Capsules responding to the following formula have been prepared:
Product of example 1; 200 mg
Excipient q.s. for a capsule finished at; 300 mg
(detail of excipient: talc, magnesium stearate, aerosil)

PHARMACOLOGICAL STUDY

Acute toxicity and behaviour

We used male mice ($CD_1$ Charles River) weighing 22–23 g and without food for 16 hours. The products were administered normally by oral route at doses of 1000–500–250 mgd/kg.

The effect of the products on the behaviour of the animals was evaluated according to the method described by Irvin (Psychopharmacologia 13,222–257, 1968) during the first 8 hours and on the 24th hour.

The mortality was checked during the 7 days following the treatment.

The $LD_{50}$ was thus found greater than 1000 mg/kg for the products of examples 1 to 3, 5, 7 to 10, 14 to 16 and 34 to 36.

Apprenticeship and memorizing

We used male mice ($CD_1$ Charles Rivers) weighing 25–30 g. The animals were placed in the illuminated part of a box with two compartments communicating by an opening (F. Barzaghi et G. Giuliani, Brit. J. Pharmacol. in course of publication).

At the instant when the mouse passes from the illuminated compartment to the dark compartment, the opening closes and the mouse is punished by an electric discharge to the paws. The animal submitted to this procedure learns to remember the punishment. In fact, if it is put back into the illuminated compartment, it will thus avoid crossing the opening and re-entering the dark compartment.

In order to induce a retrograde amnesia, the animals are submitted to an electric shock immediately after the apprenticeship. After the electric shock, the products are administered by oral route at doses of 6.25; 12.5; 25; 50; 100; 200; and 400 mg/kg.

We used 10 to 50 animals per dose.

The anti-amnesic effect of the products is evaluated 3 hours after the treatment, by using the same procedure as that used for the acquisition.

The time taken by the animal to return to the dark chamber (time limit 180 seconds) is used as the evaluation parameter.

TABLE II

| R | reaction | cryst. | chromato | F °C. | cryst. | Yield |
|---|---|---|---|---|---|---|
| pentyl | 65° C. 3 h | | $CH_3CO_2Et$ | 42–43 | | 63,4% |
| cyclopentyl | 65° C. 3 h | | $CH_3CO_2Et$ | 87–89 | 90–91° C. isopropanol | 61,7% |
| benzyl | 60° C. 3 h | n-hexane 3 benz 1 | — | 80–82 | | 72,1% |
| hexyl | 60° C. 3 h | | $CH_3CO_2Et$ | | | 68,2% |
| cyclohexyl | 60° C. 3 h | | $CH_3CO_2Et$ | 85–7 | 95–96° C. | 41,38% |

In the same experimental conditions, the control animals entered with a time lapse of 40–50 seconds.

The active products are those which cause a significant increase in the latency time with a bell-shaped dose-response curve.

The results are expressed as percentages of increase in the latency time, in comparison with the corresponding controls.

The results are given over page.

The products of examples 1 to 3, 5, 7 to 10, 12, 14, 16, 18, 31, 34 to 37 and 48 showed an anti-amnesic activity at doses between 25 and 200 mg/kg.

In particular, the products of examples 1, 14, 35, 36 and 37 induced a very notable improvement in the performance of the animals over a wide scale of doses.

TABLE III

Percentage of increase of the latency time in comparison with the controls

| Product of example | DOSE:mg/kg:os | | | | |
|---|---|---|---|---|---|
| | 200 | 100 | 50 | 25 | 12,5 |
| 1 | +109* | +132* | +118* | +95* | +79* |
| 2 | +23 | +64* | +25 | +22 | — |
| 3 | +7 | +58* | +2 | +5 | 0 |
| 5 | +75* | +44 | 0 | +11 | +28 |
| 7 | +108* | +52* | +31 | +27 | +6 |
| 8 | +75* | +53* | +41 | 0 | +24 |
| 9 | +91* | +16 | +30 | +25 | +23 |
| 10 | +65* | +18 | +21 | 0 | +14 |
| 12 | +59* | +21 | +8 | 0 | 0 |
| 14 | +98* | +99* | +47* | +42 | 0 |
| 48 | 0 | +72* | +28 | +23 | +11 |
| 15 | +65* | +39 | 0 | +14 | 0 |
| 16 | +47* | +23 | +20 | 0 | 0 |
| 31 | +75* | +79* | +65* | +31 | 0 |
| 34 | +105* | +69* | +23 | 0 | 0 |
| 35 | +65* | +72* | +95* | +54* | +4 |
| 37 | +198* | +95* | +82* | +34 | — |
| 36 | +82* | +72* | +98* | +50* | +7 |
| 18 | +88* | +49 | +36 | +21 | — |
| Pyrocetam | 20 | 48* | 10 | 19 | — |
| Antracetam | 32 | 88* | 77* | 39 | — |

*Values notably different in comparison with the controls.

We claim:
1. A compound of the formula

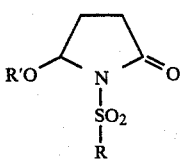

wherein R' represents a hydrogen atom, a linear, branched or cyclic alkyl radical containing up to 8 carbon atoms, an alkenyl radical containing from 2 to 8 carbon atoms, an alkanoyl radical containing from 1 to 6 carbon atoms or an aralkyl radical containing from 7 to 15 carbon atoms; and R represents an unsubstituted phenyl, or a phenyl substituted with an alkoxy radical containing up to 4 carbon atoms, an OH radical, one or more radicals selected from the group consisting of F, Cl and CF$_3$, a nitro radical, a benzyloxy radical, a phenyl radical, an NH$_2$ radical, one or more methyl radicals, a SO$_2$CH$_3$ radical, a COCH$_3$ radical, a CO$_2$CH$_3$ radical or R is a radical selected from the group consisting of

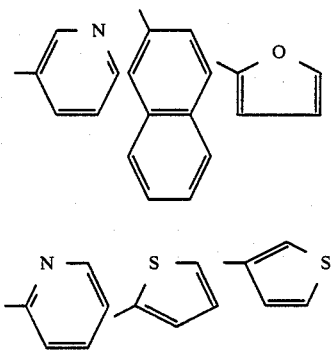

2. A compound according to claim 1, wherein R' represents a linear, branched or cyclic alkyl radical containing up to 8 carbon atoms.

3. A compound according to claim 2, wherein R' is ethyl.

4. A compound according to claim 1, which is 1-(benzenesulphonyl)-2-oxo-5-ethoxypyrrolidine.

5. A compound according to claim 1, which is 1-(4-nitrobenzenesulphonyl)-2-oxo-5-ethoxypyrrolidine.

6. A compound according to claim 1, which is 1-(benzenesulfonyl)-2-oxo-5-isopropoxypyrrolidine.

7. A compound according claim 1, which is 1-(benzenesulfonyl)-2-oxo-5-propoxypyrrolidine.

8. An anti-amnesia composition comprising an anti-amnesia effective amount of a compound according to claim 1, together with a pharmaceutically acceptable carrier.

9. An anti-amnesic composition comprising an anti-amnesia effective amount of a compound selected from the group consisting of 1-(benzenesulfonyl)-2-oxo-5-ethoxypyrrolidine, 1-(4-nitrobenzene-sulfonyl)-2-oxo-5-ethoxypyrrolidine, 1-(benzenesulfonyl)-2-oxo-5-isopropoxypyrrolidine and 1-(benzenesulphonyl)-2-oxo-5-propoxypyrrolidine, together with a pharmaceutically acceptable carrier.

10. A method for treating amnesia or memory failure which comprises administering an effective amount of a compound according to claim 1 to a patient suffering from amnesia or memory failure.

* * * * *